US006965662B2

(12) United States Patent
Eppler et al.

(10) Patent No.: US 6,965,662 B2
(45) Date of Patent: Nov. 15, 2005

(54) NONPLANAR X-RAY TARGET ANODE FOR USE IN A LAMINOGRAPHY IMAGING SYSTEM

(75) Inventors: Barry Eppler, Loveland, CO (US); Ronald K Kerschner, Loveland, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 187 days.

(21) Appl. No.: 10/321,749

(22) Filed: Dec. 17, 2002

(65) Prior Publication Data

US 2004/0114712 A1 Jun. 17, 2004

(51) Int. Cl.⁷ .......................... A61B 6/00; G01N 23/00; H01J 35/08
(52) U.S. Cl. ............................. 378/25; 378/143
(58) Field of Search ..................... 378/143, 21–27, 378/137, 144

(56) References Cited

U.S. PATENT DOCUMENTS

| | | | | |
|---|---|---|---|---|
| 2,292,859 A | * | 8/1942 | Allibone | ................... 378/137 |
| 2,343,730 A | * | 3/1944 | Atlee | ...................... 378/121 |
| 5,081,656 A | | 1/1992 | Baker et al. | |
| 5,097,492 A | | 3/1992 | Baker et al. | |
| 5,259,012 A | * | 11/1993 | Baker et al. | .................. 378/21 |
| 6,185,276 B1 | * | 2/2001 | Eastman | ..................... 378/143 |

FOREIGN PATENT DOCUMENTS

EP          0355128          5/1989

* cited by examiner

Primary Examiner—Craig E. Church
Assistant Examiner—Krystyna Suchecki (57) ABSTRACT

An x-ray laminography imaging system that utilizes a nonplanar anode target to enable objects that are oblique to the direction of projection of electron beams onto the target to be precisely imaged. Because many objects that laminography techniques are used to inspect are oblique or have portions that are oblique, the nonplanar anode target of the present invention enables enables spot patterns to be traced that are parallel to the plane of the object, regardless of whether it is oblique or orthogonal.

20 Claims, 5 Drawing Sheets

NONPLANAR X-RAY TARGET ANODE FOR USE IN A LAMINOGRAPHY IMAGING SYSTEM

TECHNICAL FIELD OF THE INVENTION

The present invention relates to x-ray imaging and, more particularly, to an x-ray laminography imaging system that utilizes a nonplanar target anode to enable oblique objects, or objects having oblique portions or features, to be imaged with preciseness.

BACKGROUND OF THE INVENTION

Laminography techniques are widely used to produce cross-sectional images of selected planes within objects. Conventional laminography requires a coordinated motion of any two of three main components of a laminography system (i.e., a radiation source, an object being inspected, and a detector). The coordinated motion of the two components can be in any of a variety of patterns, including linear, circular, elliptical and random patterns. Regardless of the pattern of coordinated motion selected, the configuration of the source, object and detector is such that any point in the object plane (i.e., the focal plane within the object) is always projected to the same point in the image plane (i.e., the plane of the detector), and any point outside the object plane is projected to a plurality of points in the image plane during a cycle of the pattern motion. In this manner, a cross-sectional image of the desired plane within the object is formed on the detector. The images of other planes within the object experience movement with respect to the detector, thus creating a blur, i.e. background, on the detector upon which the sharp cross-sectional image of the focal plane within the object is superimposed. This technique results in sharp images of the desired object focal plane. Although any pattern of coordinated motion can be used, circular patterns generally are preferred because they are more easily produced.

The laminography techniques described above are currently used in a wide range of applications including medical and industrial x-ray imaging. Laminography is particularly well suited for inspecting objects that comprise several layers, with each layer having distinguishable features. However, laminography systems that produce such cross-sectional images typically experience shortcomings in resolution and/or speed of inspection, thus accounting for the rare implementation of laminography systems for this purpose. These shortcomings are frequently due to the difficulties in achieving high speed coordinated motion of the source and detector to a degree of precision sufficient to produce a high resolution cross-section image.

In a laminography system having a field of view that is smaller than the object being inspected, it may be necessary to move the object around within the field of view to obtain multiple laminographs which, when pieced together, cover the entire object. Movement of the object is frequently achieved by supporting the object on a mechanical handling system, such as an X, Y, Z positioning table. The table is then moved to bring the desired portions of the object into the field of view. Movement in the X and Y directions locates the area to be examined, while movement in the Z directions moves the object up and down to select the plane within the object where the image is to be taken. While this method effectively enables various areas and planes of the object to be viewed, there are inherent limitations associated with the speed and accuracy of such mechanical motions. These constraints have the effect of increasing cycle time, thereby reducing the rates at which inspection can occur. Furthermore, these mechanical motions produce vibrations that tend to reduce the system resolution and accuracy.

In order to reduce or eliminate the need to move the object, and the problems associated therewith, an off-axis laminography system has been invented, which is disclosed in U.S. Pat. No. 5,259,012 (the '012 patent) and which is incorporated herein by reference in its entirety. The '012 patent discloses a laminography system in which off-axis scanning circles can be used to enable multiple locations on an object to be sequentially imaged without requiring mechanical movement of the object or of the electron beam gun that is used to generate the x-rays. The phrase "off-axis" refers to placing the center of the scan circle in a position that is not concentric with the optical axis of the imaging system. The electron beams are projected from the gun onto a metal target anode. When the electron beams impinge on the target anode, x-rays are produced. The electron beams are deflected by a voltage-controlled yoke that causes the electron beams to impinge on the target anode at selected locations to trace off-axis circles that enable different locations on the object to be scanned.

Figure 1:
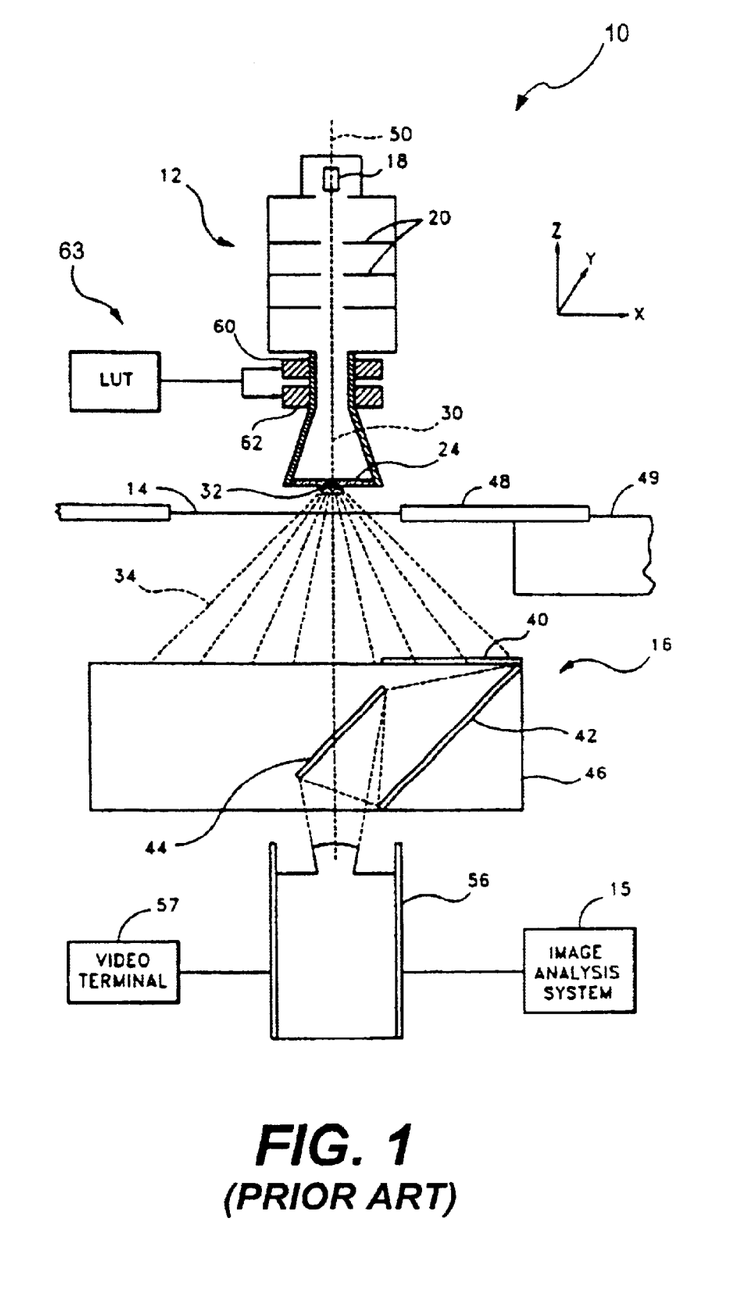
FIG. 1 is a schematic view of a known x-ray laminography system that is capable of performing off-axis scanning by steering an electron beam over a planar target anode.

FIG. 1 illustrates a schematic diagram of a laminography system 10 disclosed in the '012 patent. The system 10 comprises a source of x-rays 12 positioned above an object 14 to be imaged, and a rotating x-ray detector 16, positioned below the object 14 and opposite the x-ray source 12. The object 14 may be, for example, a printed circuit board, a manufactured item such as, for example, an aircraft part, a portion of a human body, etc. The system 10 is symmetrical about a Z-axis 50. The system 10 acquires X, Y plane cross-sectional images of the object 14 under inspection using multi-path laminography geometries, which enable multiple locations of the object 14 to be sequentially imaged without requiring mechanical movement of the object 14. In other words, off-axis (i.e., not about the axis 50, but about an axis parallel to axis 50) scanning patterns are used to image the object over different regions of the object in the X, Y plane.

The laminography system 10 may be interfaced with an analysis system 15 that automatically evaluates the cross-sectional image generated by the system 10 and provides a report to a user indicating the results of the evaluation. The source 12 is positioned adjacent the object 14, and comprises an electron gun 18, a set of electrodes 20 for electron beam acceleration and focus, a focus coil 60, a steering yoke or deflection coil 62, and a substantially flat target anode 24. An electron beam 30 emitted from the electron gun 18 along the Z-axis 50 is incident upon the target anode 24 and causes an x-ray spot 32 to be produced, which serves as an approximate point source of x-rays 34. The x-rays 34 emanate from a point on the target anode 24 where the electron beam 30 impinges upon the target anode 24. At least a portion of these x-rays pass through various regions of the object 14 and impinge on the detector 16.

The object 14 is mounted on a platform 48 which may be affixed to, for example, a granite table 49, so as to provide a rigid, vibration-free platform for structurally integrating the functional elements of the system 10, including the x-ray source 12 and the turntable 46. It is also possible that the platform 48 comprises a positioning table that is capable of moving the object 14 along three mutually perpendicular axes; labeled X, Y, and Z in FIG. 1. As stated above, with off-axis scanning, it is not necessary to physically move the object 14. However, it may be desirable to move the object 14 to some degree to improve image quality. At any rate, with off-axis scanning, it is not necessary to move the object anywhere near as much as with on-axis scanning.

The rotating x-ray detector 16 comprises a fluorescent screen 40, a first mirror 42, a second mirror 44, and a turntable 46. The turntable 46 is positioned adjacent the object 14 on the side of the object 14 opposite the x-ray source 12. A camera 56 is positioned opposite the mirror 44 for capturing images reflected into the mirrors 42, 44 from the fluorescent screen 40. The camera 56 may comprise a low light level, closed circuit television camera that produces a video image of the x-ray image formed on the fluorescent screen 40. The camera 56 may be, for example, connected to a video terminal 57 so that a user may observe the image appearing on the detector 40. The camera 56 may also be connected to the image analysis system 15.

In operation, x-rays 34 produced by the x-ray source 12 illuminate and penetrate regions of the object 14 and are intercepted by the screen 40 of detector 16. Synchronous rotation of the x-ray source 12 and detector 16 about the axis 50 causes an x-ray image of a plane within the object 14 to be formed on the detector 16. Although the axis of rotation 50 illustrated in FIG. 1 is the common axis of rotation for both the source 12 and detector 16, as stated above, these axes of rotation are not collinear in an off-axis system, but rather, are parallel to one another. The electron beam 30 is emitted from the electron gun 18 and travels in a region between the electrodes 20 and steering coils 60, 62. The steering coils 60, 62 are separate X and Y electromagnetic deflection coils that deflect the electron beam 30 discharged from the electron gun 18 in the X and Y directions, respectively.! Electrical current flowing in the coils creates a magnetic field that interacts with the electron beam 30, thereby causing the beam 30 to be deflected. The configuration of the x-ray spot pattern on the target 24 depends on where the beam 30 strikes the target 24, which depends on the manner in which the beam 30 is steered. Electrostatic deflection techniques could also be used to deflect the electron beam 30 in the desired directions.

A lookup table (LUT) 63 outputs voltage signals that are applied to the X and Y deflection coils 60, 62 to cause the electron beam spot 32 (FIG. 2) to rotate, thus producing a circular spot pattern on the surface of the target anode 24. The values stored in the LUT 63 are predetermined using a calibration technique that correlates the position of the turntable 46 (i.e., the rotational position of the detector 16 and the position of the x-ray beam spot 32). The values stored in the LUT 63 correspond to the rotational positions of the turntable 46. The turntable outputs electrical signals as it rotates that correspond to its rotational position. Once calibration has been performed using these electrical signals, the calibrated electrical signals are converted into digital values and stored the LUT 63 at appropriate addresses and off-axis laminography is then performed.

It should be noted that the target anode 24 in the '012 patent is flat. Because the target anode 24 is flat, it is difficult for the system 10 to focus on oblique objects, or oblique portions of otherwise planar objects. The term "oblique", as that term is used herein, is intended to indicate a position that is not in the X, Y plane represented by the X, Y and Z axes shown in FIG. 1. The term "planar", as that term is used herein, is intended to denote a position that is in the X, Y plane. Thus, the flat target anode 24 shown in FIG. 1 is in the X, Y plane.

Some objects, such as printed circuit boards, for example, are warped or bowed in some fashion, and therefore are oblique or have portions or features that are oblique. It would be desirable to provide an off-axis scanning system that traces circular scan patterns on a target anode in a manner similar to the manner in which the system 10 of the '012 patent operates, but that has the ability not only to precisely image planar objects, but that is also well suited for imaging oblique objects. A need exists for such a system because many objects that laminography techniques are used to inspect are oblique or have portions that are oblique. In addition, such a system could increase the types of objects that can be precisely imaged using laminography.

SUMMARY OF THE INVENTION

The present invention provides an x-ray laminography imaging system that utilizes a stationary x-ray source and generates a moving pattern of x-ray spots on a nonplanar target anode synchronously with rotation of an x-ray detector. Because the target anode is nonplanar, objects that are oblique, or oblique portions of generally planar objects, can be precisely imaged.

The x-ray laminography imaging system comprises an electron beam source that projects a beam of electrons along a Z-axis of the system, a nonplanar anode target upon which the electron beam impinges, an electron beam deflection controller that controls the deflection of the beam of electrons produced by the electron beam source onto the anode target, and an x-ray detector that receives x-rays that emanate from the target and pass through the object and converts the received x-rays into electrical signals from which an image of at least a portion of the object can be constructed. The electron beam deflection controller causes the electron beams to be deflected in an X-direction and a Y-direction in a selected manner so that the beam of electrons impinges on the target at particular locations on the target to produce x-ray spot paths having selected configurations. The X-direction and the Y-direction are perpendicular to each other and perpendicular to the Z-direction. The configurations of the x-ray spot paths are selected based on the plane in which the object being imaged lies with respect to the X, Y and Z-directions.

The present invention also provides a method of performing x-ray laminography. The method comprises the steps of projecting a beam of electrons along a Z-axis of the system from an electron beam source onto a nonplanar metallic anode target at particular locations on the target to produce paths of x-ray spots having selected configurations. X-rays emanate from the target at the locations of the spots on the target.

Deflecting the beam of electrons produced by the electron beam source with an electron beam deflection controller to cause the electron beams to be deflected in an X-direction and a Y-direction in a selected manner so that the electron beams impinge on the target at particular locations on the target to produce x-ray spot paths having selected configurations, the X-direction and the Y-direction being perpendicular to each other and perpendicular to the Z-direction; and selecting the configurations of the x-ray spot paths based on a plane in which an object being imaged lies with respect to the X, Y and Z-directions.

These and other features and advantages of the present invention will become apparent from the following description, drawings and claims.

DETAILED DESCRIPTION OF THE PREFERRED EMBODIMENTS

Figure 2:
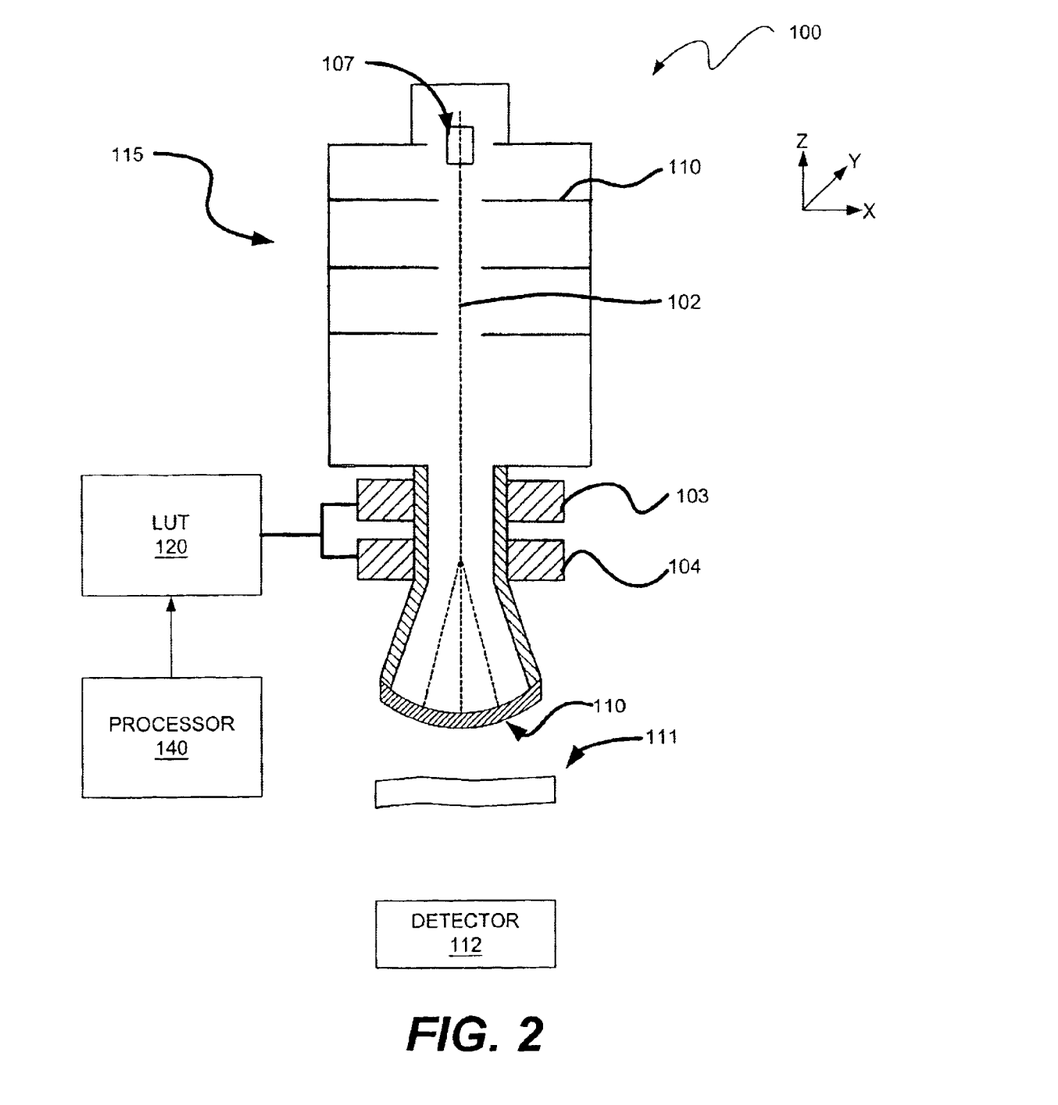
FIG. 2 is a schematic view of the laminography system of the present invention comprising a nonplanar target anode that enables laminography to be used to precisely image oblique objects.
Figure 3:
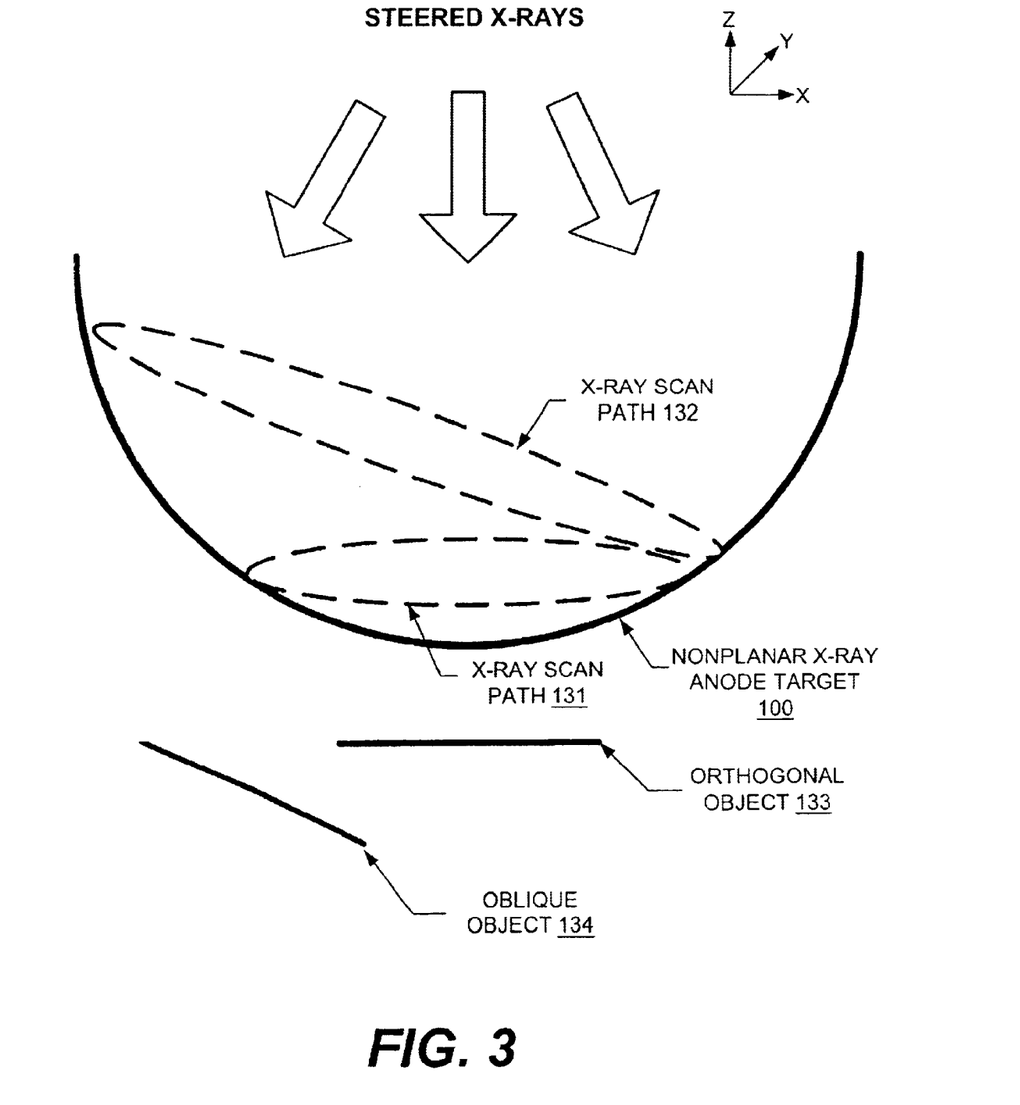
FIG. 3 is a schematic view of the nonplanar target anode of the present invention in accordance with an example embodiment.
Figure 5:
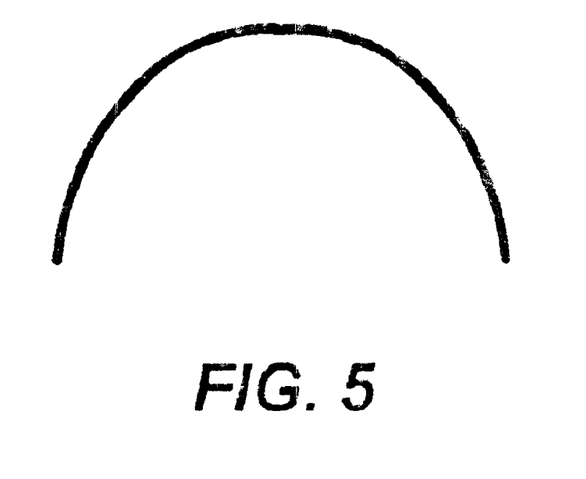
FIG. 5 illustrates a target anode that is concave in shape.
Figure 6:
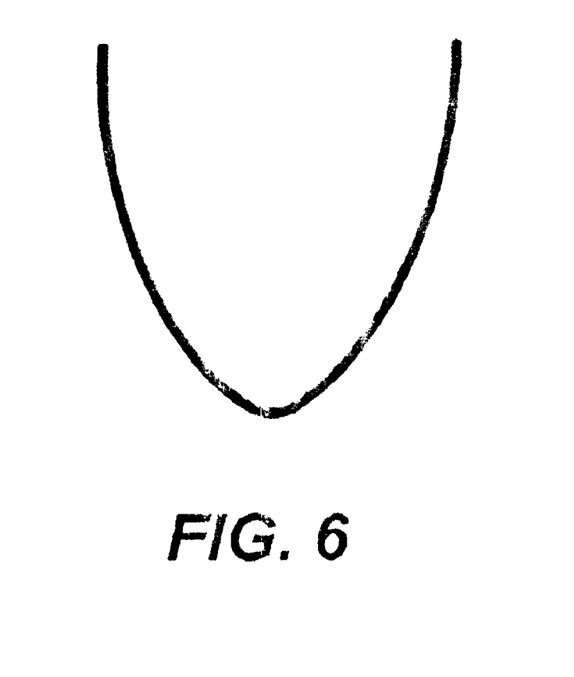
FIG. 6 illustrates a target anode that is parabolic in shape.

FIG. 2 is a schematic view of the laminography system 100 of the present invention, which comprises a nonplanar target anode 110 that enables oblique objects to be precisely imaged. The laminography system 100 of the present invention may be, but need not be, identical in all respects to the laminography system 10 shown in FIG. 1, with the exception that the target anode 110 of the laminography system 100 of the present invention is nonplanar. The shape of the nonplanar target anode 110 of the present invention is not limited to any particular shape, but preferably is symmetrical. The target anode 110 may have, for example, a convex spherical shape, as shown in FIGS. 2 and 3, a concave shape, as shown in FIG. 5, a parabolic shape, as shown in FIG. 6, etc. Preferably, the nonplanar target anode 110 has the shape of an axially symmetric shell of revolution about the Z-axis.

The electrodes 101 and coils 103 and 104 produce electromagnetic fields that interact with the electron beam 102 to focus and direct the beam 102 onto the nonplanar target anode 110, thereby forming an electron beam spot on the nonplanar target anode 110 from which x-rays are emitted, at least some of which pass through the object 111 and impinge on x-ray detector 112. The steering coils 103 and 104 enable the x-ray source 115 to provide x-rays from the x-ray spots on the nonplanar target anode 110 such that the locations of the spots move in a desired pattern around the nonplanar target anode 110. It is the creation of the desired x-ray spot patterns on the nonplanar target anode 110 that eliminate or reduce the need to physically move the object 111 to obtain images of different regions of the object 111 in the X, Y plane in different Z-planes, and in planes that are at oblique angles to the X, Y plane.

As indicated above with reference to FIG. 1, electrical current flowing in the steering coils 103 and 104 creates a magnetic field that interacts with the electron beam 102, thereby causing the beam 102 to be deflected. The configuration of the x-ray spot pattern on the nonplanar target anode 110 depends on the where the beam 102 strikes the target 110, which depends on the manner in which the beam 102 is steered. A lookup table (LUT) 120 can be used to store voltage values that are applied to the X and Y deflection coils 103 and 104 to cause the electron beam spot to rotate, thus producing a circular spot pattern on the surface of the nonplanar target anode 110. Although a LUT is preferred, any memory device may be used for this purpose. The laminography system 100 also comprises a processor 140 of some type that is programmable to cause the stored values to be read out and applied to the deflection coils 103 and 104 in a particular order to produce circular spot patterns having preselected configurations. The values that are read out of memory will be converted into analog values by a digital-to-analog converter (not shown), and preferably amplified by an amplifier (not shown) before being applied to the deflection coils 103 and 104.

As shown in FIG. 2, the object 111 being imaged is somewhat warped or bowed. In other words, any given cross-section of the object 111 is not entirely in the same X, Y plane. For this reason, alterations in spot patterns generated on a flat anode target, such as target 24 of the system 10 shown in FIG. 1, will not precisely image all regions of the object 111. In accordance with the present invention, various circles of given radius are traced on the nonplanar anode target 110 to ensure that the spot pattern is coplanar with the object 111. Furthermore, in addition to providing spot patterns having orientations that can be changed to ensure that the path of the spot is coplanar with the object 111, the nonplanar anode target also provides the ability to vary the axial position of the spot path in the Z-direction, which facilitates changes in focus and magnification.

FIG. 3 is a diagram illustrating first and second scan paths 131 and 132 formed by tracing spots on the nonplanar target 100 that are coplanar with an orthogonal object 133 (i.e., an object in the X, Y plane) and with an oblique object 134, respectively. The nonplanar anode target 100 in this example embodiment is a concave, semi-spherical shell that is axially symmetric about the Z-axis of the system, which is co-linear with the electron beam 102. It can be seen that the scan path 131 is in an X, Y plane as is the orthogonal object 132. Therefore, scan path 131 is in a plane that is parallel to the plane in which the orthogonal object 133 lies. The x-ray scan path 132 is not in an X, Y plane, but is oblique. Likewise the oblique object 134 is not in an X, Y plane. However, the plane of the scan path 132 is parallel to the plane of the oblique object 133. Therefore, the scan path 131 will cause the orthogonal object 133 to be precisely imaged, but would not result in the oblique object 134 being precisely imaged. Likewise, the scan path 132 will cause the oblique object 134 to be precisely imaged, but would not result in the orthogonal object 133 being precisely imaged.

By steering the electron beam in the appropriate manner, spot paths that are parallel to the plane of the object can always be traced, which means that the object of interest can always be precisely imaged, regardless of whether it is orthogonal or oblique to some degree.

Figure 4:
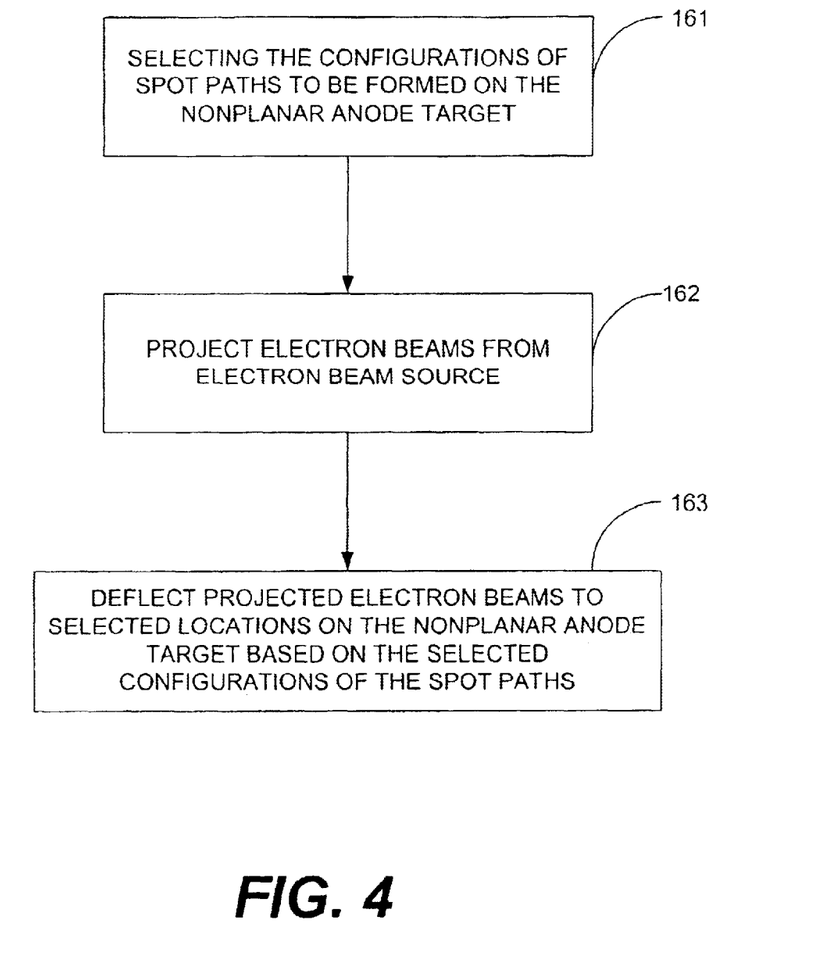
FIG. 4 is a flow chart illustrating the method of the present invention in accordance with an embodiment.

The method of the present invention will now be described with reference to FIG. 4. The configurations of the spot paths to be formed on the nonplanar anode target 100 are preselected, as indicated by block 161, based on the shape of the target (e.g., whether it is orthogonal, oblique, degree of obliqueness, etc.). The preselected spot paths will correspond to the preselected values to stored in the LUT 120. After the spot paths to be formed on the target have been selected and the corresponding values have been stored in the LUT 120, the object is imaged by projecting the beam of electrons 102 from the electron beam source 107 onto the target 100, as indicated by block 162. The beam of electrons 102 is deflected by the deflection coils 103 and 104 in the manner dictated by the values read out of the LUT 120 to cause the spot patterns to be appropriately formed on the target 100 so that the object is precisely imaged, as indicated by block 163.

It should be noted that the present invention has been described only with reference to preferred embodiments for example purposes and in the interest of brevity, and that the present invention is not limited to these embodiments. Those skilled in the art will understand, in view of the present disclosure, the manner in which embodiments not disclosed herein can be developed by utilizing the principles and concepts of the present invention. These undisclosed embodiments are also within the scope of the present invention. Those skilled in the art will also understand that modifications can be made to the embodiments discussed herein and that all such modifications are within the scope of the present invention.

What is claimed is:

1. An x-ray laminography imaging system that generates a moving pattern of x-ray spots on a nonplanar metallic anode target synchronously with rotation of an x-ray detector to reduce or eliminate the need to move an object being imaged, the system comprising:

an electron beam source, the electron beam source projecting a beam of electrons along a Z-axis of the system;

a nonplanar metal anode target, the electron beams projected by the electron beam source impinging on the target at particular locations on the target to produce paths of x-ray spots having selected configurations, and wherein x-rays emanate from the target at the locations of the spots on the target;

an electron beam deflection controller, the electron beam deflection controller controlling the deflection of the beam of electrons produced by the electron beam source to cause the electron beams to be deflected in an X-direction and a Y-direction in a selected manner so that the electron beams impinge on the target at particular locations on the target to produce x-ray spot paths having selected configurations, the X-direction and the Y-direction being perpendicular to each other and perpendicular to the Z-direction, and wherein the configurations of the x-ray spot paths are selectable to be in a plane oblique to an X-Y plane and substantially parallel to a selected of a region to be imaged with respect to the X, Y and Z-directions; and an x-ray detector, the detector receiving x-rays that emanate from the target and pass through the object and converting the received x-rays into electrical signals from which an image of at least a portion of the object can be constructed.

2. The system of claim 1, wherein the electron beam deflection controller is programmable.

3. The system of claim 2, wherein the electron beam deflection controller includes a memory device having selected digital values stored at selected address locations therein, a processor, a digital-to-analog converter (DAC), and X and Y deflection coils of a deflection yoke, the processor being programmed to cause the digital values stored in the memory device to be read out of the memory device in a selected order, such that each value read out of the memory device is converted into an analog electrical signal by the DAC and applied to the deflection yoke to cause the beam of electrons to be deflected in a selected manner so that the beam impinges on the target at particular locations on the target to produce the x-ray spot paths having the selected configurations.

4. The system of claim 1, wherein the nonplanar metal anode target is axially symmetric about the Z-axis.

5. The system of claim 4, wherein the target is convex with respect to the direction of projection of the beam of electrons.

6. The system of claim 4, wherein the target is concave with respect to the direction of projection of the beam of electrons.

7. The system of claim 4, wherein the target is generally parabolic in shape.

8. An nonplanar metallic target anode in an x-ray laminography imaging system, the system comprising an electron beam source that projects a beam of electrons along a Z-axis of the system x-ray laminography imaging system, and an electron beam deflection controller that controls the deflection of the beam of electrons to cause the electron beams to be deflected in a selected manner in an X-axis direction and a Y-axis direction, the X-axis and Y-axis being perpendicular to each other and perpendicular to the Z-axis so that the beam of electrons impinges on the target at selected locations to produce x-ray spot paths having selected configurations, wherein the configurations of the x-ray spot paths are selectable to be in a plane oblique to an X-Y plane and substantially parallel to a selected plane of a region to be imaged.

9. The target of claim 8, wherein the target is axial symmetric about the Z-axis.

10. The target of claim 8, wherein the target is convex with respect to the direction of projection of the beam of electrons.

11. The target of claim 8, wherein the target is concave with respect to the direction of projection of the beam of electrons.

12. The system of claim 8, wherein the target is generally parabolic in shape.

13. A method of performing x-ray laminography using an x-ray laminography imaging system, the method comprising the step of projecting a beam of electrons along a Z-axis of the system from an electron beam source onto a nonplanar metallic anode target at particular locations on the target to produce paths of x-ray spots having selected configurations, and wherein x-rays emanate from the target at the locations of the spots on the target, wherein the configurations of the x-ray spot path are selectable to be in a plane oblique to an X-Y plane and substantially parallel to a selected plane of a region to be imaged.

14. The method of claim 13, further comprising the steps of:

deflecting the beam of electrons produced by the electron beam source with an electron beam deflection controller to cause the electron beams to be deflected in an X-direction and a Y-direction in a selected manner so that the electron beams impinge on the target at particular locations on the target to produce x-ray spot paths having selected configurations, the X-direction and the Y-direction being perpendicular to each other and perpendicular to the Z-direction; and selecting the configurations of the x-ray spot paths to be in a plane oblique to an X-Y plane substantially parallel to a selected of a region to be imaged with respect to the X, Y and Z-directions.

15. The method of claim 14, wherein the electron beam deflection controller is programmable.

16. The method of claim 15, wherein the electron beam deflection controller includes a memory device having selected digital values stored at selected address locations therein, a processor, a digital-to-analog converter (DAC), and X and Y deflection coils of a deflection yoke, the processor being programmed to cause the digital values stored in the memory device to be read out of the memory device in a selected order, such that each value read out of the memory device is converted into an analog electrical signal by the DAC and applied to the deflection yoke to cause the beam of electrons to be deflected in a selected manner so that the beam impinges on the target at particular locations on the target to produce the x-ray spot paths having the selected configurations.

17. The method of claim 14, wherein the nonplanar metal anode target is axial symmetric about the Z-axis.

18. The method of claim 14, wherein the target is convex with respect to the direction of projection of the beam of electrons.

19. The method of claim 14, wherein the target is concave with respect to the direction of projection of the beam of electrons.

20. The method of claim 14, wherein the target is generally parabolic in shape.

* * * * *

UNITED STATES PATENT AND TRADEMARK OFFICE
CERTIFICATE OF CORRECTION

PATENT NO. : 6,965,662 B2 Page 1 of 1
APPLICATION NO. : 10/321749
DATED : November 15, 2005
INVENTOR(S) : Eppler et al.

It is certified that error appears in the above-identified patent and that said Letters Patent is hereby corrected as shown below:

On the face page, in field (54), in "Title", in column 1, line 1, -- A -- before "NONPLANAR".

In column 7, line 27, in Claim 1, after "selected" insert -- plane --.

In column 8, line 23, in Claim 13, after "spot" delete "path" and insert -- paths --, therefor.

In column 8, line 39, in Claim 14, after "selected" insert -- plane --.

Signed and Sealed this

Fifteenth Day of August, 2006

JON W. DUDAS
*Director of the United States Patent and Trademark Office*